United States Patent [19]

Andersen

[11] Patent Number: 5,057,091

[45] Date of Patent: Oct. 15, 1991

[54] ENTERAL FEEDING TUBE WITH A FLEXIBLE BOLUS AND FEEDING BOLUS

[75] Inventor: Erik Andersen, Vernon Hills, Ill.

[73] Assignee: Corpak, Inc., Wheeling, Ill.

[21] Appl. No.: 387,866

[22] Filed: Jul. 31, 1989

[51] Int. Cl.[5] ........................................ A61M 31/00

[52] U.S. Cl. ................................................ 604/270

[58] Field of Search ............... 604/270, 275, 280, 283; 128/658

[56] References Cited

U.S. PATENT DOCUMENTS

| | | | |
|---|---|---|---|
| 1,899,781 | 2/1933 | Twiss . | |
| 3,189,031 | 6/1965 | Andersen | 604/270 |
| 3,395,710 | 8/1968 | Stratton et al. | 604/270 |
| 4,410,320 | 10/1983 | Dykstra et al. | 604/270 |
| 4,490,143 | 12/1984 | Quinn et al. | 604/270 |
| 4,594,074 | 6/1986 | Andersen et al. | 604/270 |
| 4,610,673 | 9/1986 | Russo | 604/270 |
| 4,613,323 | 9/1986 | Norton | 604/270 |
| 4,654,036 | 3/1987 | Tolkoff | 604/270 |
| 4,778,455 | 10/1988 | Kousai et al. | 604/270 |
| 4,781,704 | 11/1988 | Potter | 604/270 |

*Primary Examiner*—John D. Yasko
*Assistant Examiner*—Anthony Gutowski
*Attorney, Agent, or Firm*—Wallenstein, Wagner & Hattis, Ltd.

[57] ABSTRACT

An enteral feeding tube adapted for transpyloric passage and duodenal intubation of a distal end of the feeding tube in a patient capable of peristaltic contractions of the stomach wall. A flexible bolus is located at the distal end of the feeding tube, which has a feeding bolus and connected thereto by a linking means. The flexible bolus is of such length, diameter and deformability to initiate peristaltic movement of the stomach wall. The linking means is of outer dimensions smaller than the outer dimensions of the flexible bolus and the feeding tube, and is of a length, diameter and deformability selected to initiate and maintain peristaltic contractions in the stomach walls around and behind the flexible bolus. The continued peristaltic contractions act upon the flexible bolus and linking means, thereby drawing the feeding bolus and distal end of the feeding tube through the pylorus to achieve duodenal intubation.

7 Claims, 2 Drawing Sheets

ENTERAL FEEDING TUBE WITH A FLEXIBLE BOLUS AND FEEDING BOLUS

TECHNICAL FIELD OF THE INVENTION

The present invention generally relates to the field of enteral therapy, and, in particular, to an improved enteral feeding tube to achieve transpyloric passage and, thereby, duodenal intubation.

BACKGROUND OF THE INVENTION

Enteral therapy is a method of nutritional support achieved typically through pre-pyloric intubation of a nasoenteric feeding tube. Tracheobronchial aspiration, which may lead to esophageal regurgitation, has been recognized as a risk of intragastric or pre-pyloric tube feeding. Post-pyloric intubation of the enteral feeding tube has been identified as a means of reducing the risk of tracheobronchial aspiration and esophageal regurgitation. To effect post-pyloric or duodenal intubation, it is necessary to obtain transpyloric passage of the distal end of the feeding tube. This may be achieved by endoscopy, fluoroscopy or x-ray techniques for uncooperative or comatose patients, or those patients having impaired peristaltic movement within the gastrointestinal tract. Preferably, however, transpyloric passage is most safely achieved by use of peristaltic movement of the stomach walls to cause the distal end of the feeding tube to migrate through the pylorus.

A recent study has suggested that there is no advantage in distally weighted feeding tubes as opposed to unweighted feeding tubes in achieving transpyloric passage and duodenal intubation. Levenson, R. et al., Do Weighted Nasoenteric Feeding Tubes Facilitate Duodenal Intubations?, Journal of Parenteral and Enteral Nutrition, vol. 12, pp. 135–137 (1988). However, not only does this study use an unusually large, and therefore, stiff 10 Fr. tube, it also acknowledges that the effect of various weighted bolus designs on duodenal intubations was not evaluated. It is an object of the present invention to develop a distally weighted feeding tube which maximizes use of peristaltic contractions to obtain a high incidence of successful transpyloric passage.

SUMMARY OF THE INVENTION

According to the present invention, an enteral feeding tube has been developed which is especially adapted for achieving passive duodenal intubation through use of peristaltic movement of the stomach walls. In all embodiments of the present invention, a bolus is joined to a distal end of an enteral feeding tube by a linking means comprised of a length of flexible material of a diameter smaller than either the bolus or the feeding tube. The feeding tube is inserted through the patient's nasal passages and is guided through the patient's stomach by the use of a stylet. Upon reaching the pylorus after passing through the stomach, intubation is stopped. Preferably, natural peristaltic movements of the stomach walls are utilized to obtain passage of the bolus through the pylorus. Where peristalsis does not occur, such as after gastric surgery, endoscopy or fluoroscopy techniques may be utilized to achieve transpyloric passage.

The bolus and the linking means connecting the bolus to the distal end of the feeding tube are also of such length, diameter and deformability to permit the peristaltic action of the stomach to act upon the bolus and linking means to draw them through the pylorus. Due to the fine diameter and high deformability characteristics of the linking means, it is believed that peristaltic action responds to the bolus in the same manner as a free-floating independent mass. That is, the linking means enhances peristalsis by initiating and permitting contractions to continue behind the bolus to draw the bolus through the pylorus. Continued peristaltic action results in passage of the distal end of the feeding tube into the duodenum through the pylorus, whereby the feeding tube is placed in a position to allow nutritional fluid to flow directly into the duodenum through one or more openings in the distal end of the feeding tube. It is well known in the art that such post-pyloric feeding lessens the incidence of tracheobronchial aspiration and esophageal regurgitation.

In the preferred embodiment of the present invention, the bolus is weighted with a non-toxic mass, and the inside surface of the bolus is coated with a radiopaque material to make the bolus better appear on a fluoroscope or on x-rays. This radiopaque coating results in an improved ability to track the bolus as it is moved through the patient's gastrointestinal tract to more easily determine whether transpyloric passage of the bolus and the feeding tube have been successfully achieved.

In another embodiment of the present invention, the bolus and linking means are both hollow. This permits insertion of a stylet through the feeding tube, linking means and bolus to eliminate any pre-pyloric looping of the bolus and linking means, and allows passage of nutritional fluid into the duodenum through the distal end of the bolus from the feeding tube. This also obviates the need for the distal end of the feeding tube to pass through the pylorus.

Other advantages and aspects of the invention will become apparent upon making reference to the specification, claims, and drawings to follow.

DETAILED DESCRIPTION OF THE INVENTION

Figure 1:
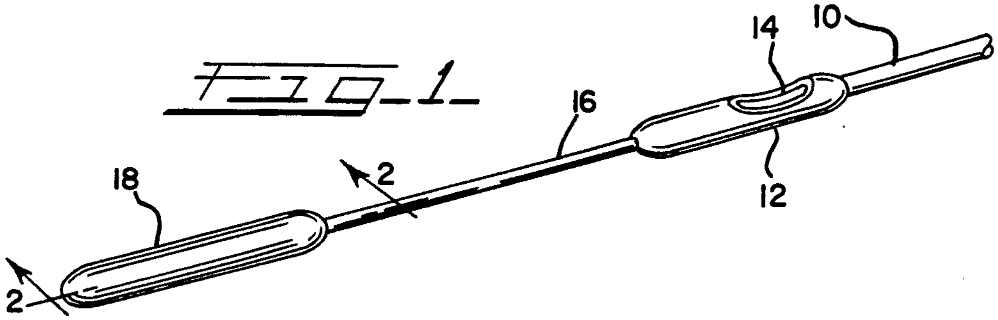
FIG. 1 discloses in a perspective view one embodiment of a distal end bolus for a feeding tube for duodenal intubation.

While this invention is susceptible of embodiment in many different forms, there is shown in the drawings and will be described in detail, a preferred embodiment of the invention. The present disclosure is to be considered only as an exemplification of the principles of the invention and is not intended to limit the broad aspect of the invention to the embodiment illustrated.

Referring now to the drawings, FIG. 1 discloses an embodiment of the present invention which comprises an enteral feeding tube 10 preferably having, at its distal end, a feeding bolus 12 having a non-occluding high flow outlet 14 as taught in U.S. Pat. No. 4,594,074. A second bolus 18 is connected to the distal end of the feeding tube 10 by a linking means 16. Bolus 18, preferably, may be weighted with a non-toxic mass such as tungsten discs or cylinders. Bolus 18 should be of such length, diameter and deformability so as to initiate peristaltic movement in the distal inner walls of the stomach 30 near the pylorus 24. Linking means 16 must be of a significantly different length, diameter and deformability than bolus 18 to maintain peristaltic movements of the stomach walls, and thereby draw the bolus 18, linking means 16 and feeding bolus 12 through the pylorus 24 and into the duodenum 28. The linking means 16 should also be of greater flexibility than that of the feeding tube 10 to allow peristaltic movements of the stomach walls to act upon the linking means 16 to advance it through the pylorus 24.

Feeding bolus 12, at the distal end of the feeding tube 10, has an opening 14 to allow nutritional fluid passed through the feeding tube 10 to enter the duodenum 28 after the feeding bolus 12, linking means 16, and the opening 14 have achieved transpyloric passage as a result of the peristaltic action of the stomach walls upon the bolus 18 and linking means 16. Feeding bolus 12 is to be more rigid than feeding tube body 10.

Figure 2:
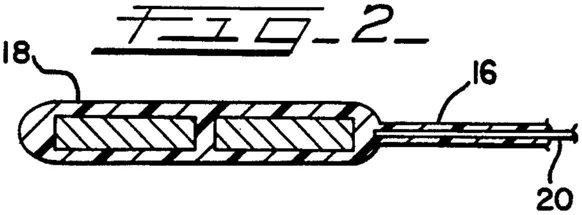
FIG. 2 discloses a sectional view taken along line 2—2 of FIG. 1.

FIG. 2 discloses a cross-section of the bolus 18. The bolus 18 may be hollow or solid as long as it is of the required length, diameter and deformability to initiate and maintain peristaltic movements of the stomach walls. The bolus 18 may also, preferably, be coated on the inside with a radiopaque material such as barium sulfate ($BaSO_4$) or bismuth trioxide ($Bi_2O_3$) to make the bolus 18 more easily visible on a fluoroscope or on x-rays while being intubated through the patient's gastrointestinal tract.

FIG. 2 also discloses linking means 16 as being hollow in order to receive a stylet or guide wire 20. Due to the high degree of flexibility and deformability of linking means 16, stylet 20 imparts sufficient rigidity to linking means 16 to provide adequate manipulation during pre-pyloric intubation of the present invention.

Figure 3:
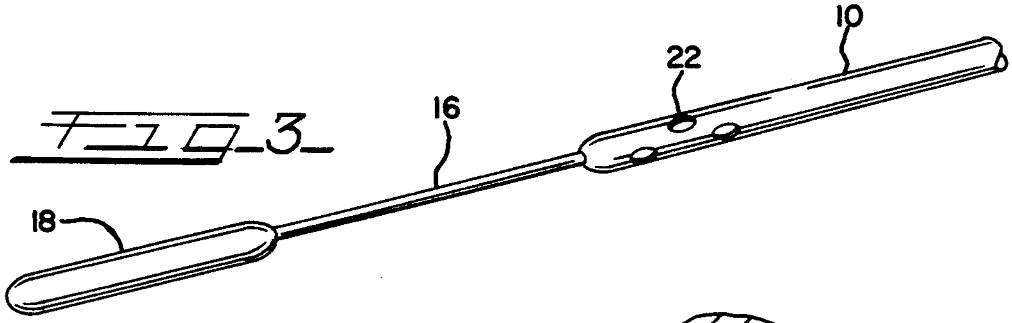
FIG. 3 discloses in a perspective view another embodiment of the present invention.

FIG. 3 discloses an embodiment of the present invention wherein one or more openings 22 are placed at the distal end of the feeding tube 10 to allow nutritional fluid to pass through the opening 22 directly into the duodenum 28 once the distal end of the feeding tube 10 has achieved transpyloric passage. This embodiment obviates the need for the feeding bolus 12 at the distal end of the feeding tube 10 as shown in the previous embodiment of FIG. 1.

Figure 4:
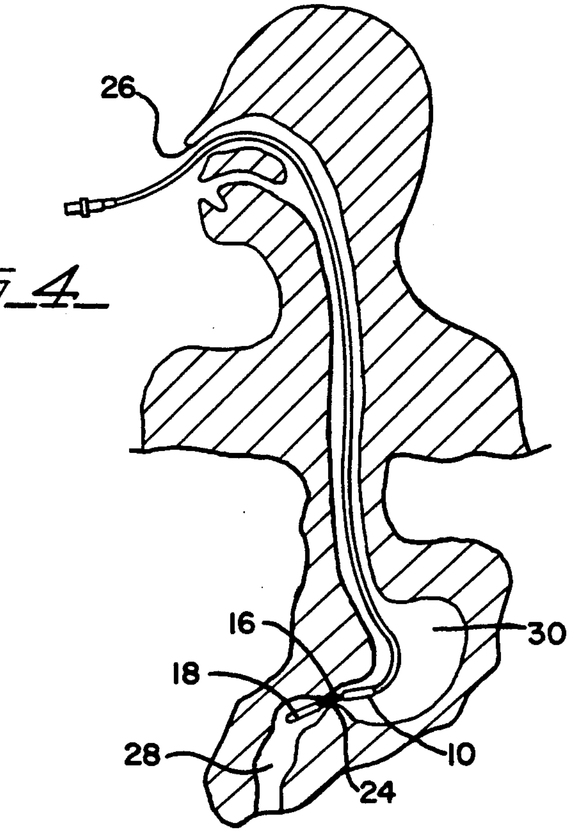
FIG. 4 is an illustration depicting one stage of duodenal intubation in which the bolus has achieved transpyloric passage.

FIG. 4 illustrates the passage of the bolus 18 and linking means 16 through the pylorus 24. The present invention is intubated, using a stylet 20, into the patient's nasal passages 26 and directed through the stomach 30 to a point just before the pylorus 24. Natural peristaltic actions of the stomach walls will then be initiated by the presence of the bolus 18 to act upon the bolus 18 and linking means 16 to draw the distal end of the feeding tube 10 through the pylorus 24. Nutritional fluid may then be dispensed directly into the duodenum 28 through the openings 22 in the distal end of the feeding tube 10.

Figure 5:
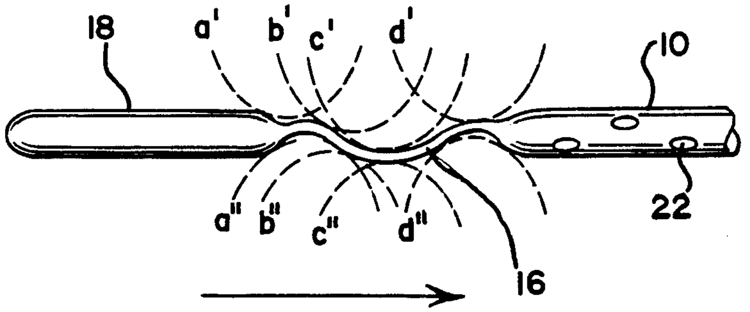
FIG. 5 discloses the progressive deformation of the linking means by peristaltic movement of the stomach and pylorus; and, FIG. 6 discloses in a perspective view a further embodiment of the present invention.

FIG. 5 discloses the progressive deformation of the linking means 16 while it is being acted upon by peristaltic contractions of the stomach walls and duodenum 28, such peristalsis draws the bolus 18 and the linking means 16 through the pylorus 24 into the duodenum 28 and allowing the distal end of the feeding tube 10 to pass through the pylorus 24. The parabolas a', b', c' and d' show the deformation of the linking means 16 caused by the peristaltic contractions of the muscles along the stomach walls while the linking means 16 is being advanced through the pylorus 24 to achieve duodenal intubation of the feeding tube 10.

Figure 6:
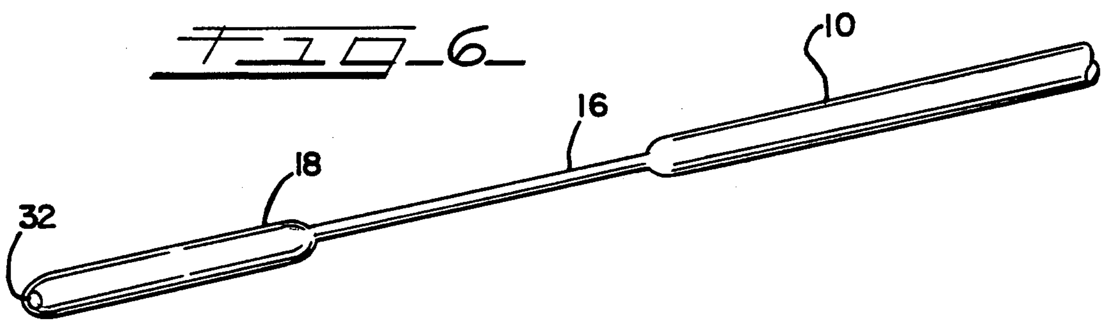

FIG. 6 discloses a further embodiment of the present invention wherein both the bolus 18 and linking means 16 are hollow, and the bolus 18 has one or more openings 32 at its distal end, to permit nutritional fluid flowing from the feeding tube 10 to pass directly into the duodenum 28 through the linking means 16 and bolus 18 after the bolus 18 has passed through the pylorus 24. This embodiment obviates the need for openings at the distal end of the feeding tube 10, and for the distal end of the feeding tube 10 to pass through the pylorus 24. This further embodiment also allows the stylet 20 to pass through the linking means 16 and bolus 18 to eliminate looping of the bolus 18 and linking means 16 during pre-pyloric intubation.

While the specific embodiments have been illustrated and described, numerous modifications come to mind without significantly departing from the spirit of the invention and the scope of protection is only limited by the scope of the accompanying claims.

I claim:

1. An enteral feeding tube adapted for transpyloric passage and duodenal intubation of a distal end of said feeding tube in a patient capable of peristaltic contractions of the stomach wall, comprising:
   a. a feeding tube having a distal end;
   b. a feeding bolus located at the distal end of said feed tube, said feeding bolus having at least one opening in fluid communication with said feeding tube for dispensing nutritional fluids, and being of greater rigidity than said feeding tube;
   c. an elongated, generally flexible bolus, said flexible bolus extending from said feeding bolus; and,
   d. means for linking said flexible bolus to the feeding bolus of said feeding tube, said linking means having outer dimensions smaller than the outer dimensions of said flexible bolus and said feeding bolus, said linking means being of a length, diameter and deformability selected to initiate and maintain peristaltic contractions in the stomach walls around and behind said flexible bolus, the peristaltic contractions acting upon and advancing said flexible bolus, linking means, feeding bolus, and distal end of said feeding tube through the pylorus to achieve duodenal intubation.

2. The enteral feeding tube of claim 1 wherein said linking means comprises an 8 Fr. or smaller diameter tube.

3. The enteral feeding tube of claim 1 wherein said flexible bolus is weighted with a non-toxic mass.

4. The enteral feeding tube of claim 2 wherein said flexible bolus is weighted with a non-toxic mass.

5. The enteral feeding tube of claims 1, 2, 3 or 4 wherein the inside surface of said flexible bolus is coated with a radiopaque material.

6. The enteral feeding tube of claim 5 wherein said radiopaque material is bismuth trioxide.

7. The enteral feeding tube of claim 5 wherein said radiopaque material is barium sulfate.

* * * * *